United States Patent [19]

Salem et al.

[11] 4,097,577

[45] Jun. 27, 1978

[54] METHOD OF LOWERING INTRAOCULAR PRESSURE WITH ANTAZOLINE

[75] Inventors: Harry Salem, Elkins Park; Domingo M. Aviado, Wynnewood, both of Pa.

[73] Assignee: Cooper Laboratories, Incorporated, Parsippany, N.J.

[21] Appl. No.: 713,805

[22] Filed: Aug. 12, 1976

[51] Int. Cl.² ............................................. A01N 9/22
[52] U.S. Cl. ................................................ 424/273 R
[58] Field of Search ........................................ 424/273

[56] References Cited

PUBLICATIONS

New Drugs, (1966), published by American Medical Assoc., pp. 327–335.
Wilson et al., Textbook of Organic Medicinal & Pharmaceutical Chemistry, (1962), p. 553.
Louyot, Chemical Abstracts 47:7674a, (1953).

*Primary Examiner*—Stanley J. Friedman
*Assistant Examiner*—D. W. Robinson
*Attorney, Agent, or Firm*—Thomas R. Boland; John J. Kolano

[57] ABSTRACT

A method for lowering intraocular pressure in mammals by administering thereto an effective amount of antazoline, i.e., 2-(N-benzylanilinomethyl)-2-imidazoline or its pharmacologically acceptable acid addition salts, preferably antazoline phosphate.

3 Claims, No Drawings

METHOD OF LOWERING INTRAOCULAR PRESSURE WITH ANTAZOLINE

BACKGROUND OF THE INVENTION

This invention relates to a method for treating ocular hypertension in mammals and more particularly to a method for lowering intraocular pressure in mammals by administering thereto an effective amount of antazoline.

Ocular hypertension is associated with glaucoma, a disease of the eye which is characterized by a progressive increase in intraocular pressure. If left untreated, such increased pressure will ultimately damage the optic nerve of the eye so that blindness results. Thus, a common treatment for glaucoma is the administration to the diseased eye of a substance which is effective in lowering such intraocular pressure. Several substances are currently used for this purpose, including epinephrine, pilocarpine and physostigmine, but each such substance has been shown to have unwanted side effects, thus promoting the search for new drugs. U.S. Pat. No. 3,933,998 describes the ocular hypotensive effect of one such drug, 4 [2-(isopropylamine)ethyl]pyrocatechol, and reviews the attempts of others to develop therapeutically effective substances.

SUMMARY OF THE INVENTION

According to this invention, a method is provided for reducing the intraocular pressure in mammals which comprises administering thereto an effective amount of a compound selected from the group consisting of antazoline and ophthalmologically acceptable acid addition salts thereof. Pharmaceutical compositions comprising such an acid addition salt of antazoline and a non-toxic, pharmaceutically acceptable, ophthalmological carrier are particularly suitable for use in this invention. Such compositions will include ophthalmic solutions and ointments. However, the preferred form of this invention comprises administering to a mammilian eye an effective amount for reducing intraocular pressure of antazoline phosphate, usually in an aqueous ophthalmic solution.

DETAILED DESCRIPTION OF THE INVENTION

As indicated above, this invention comprises a method for reducing intraocular pressure in mammals through the use of antazoline, preferably by topical administration to the mammalian eye of an effective ophthalmologically acceptable amount of antazoline phosphate.

Antazoline, i.e., 2-(N-benzylanilinomethyl)-2-imidazoline, is a compound of the ethylenediamine type which is commonly used as an antihistamine for local and generalized allergic reactions. It may be prepared by the condensation of benzylaniline with 2-(chloromethyl)imidazoline in the manner described by Miescher et al. in U.S. Pat. No. 2,449,241. In the preferred form of its phosphate salt it is soluble in water and may be represented by the following formula:

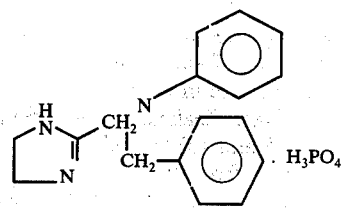

According to this invention, antazoline phosphate, for example, will be topically administered to mammalian eyes in the form of a composition comprising such antazoline phosphate, in a chemically equivalent amount of from about 0.5% to about 4.0% by weight of the base form of antazoline, and a non-toxic, pharmaceutically acceptable, ophthalmological carrier therefor. Preferably, the carrier is an aqueous isotonic vehicle including, for example, 0.9% sodium chloride; although an isotonically equivalent vehicle such as 1.9% boric acid aqueous solution will also be satisfactory. The amount of such a composition delivered to each eye will be sufficient to deliver an effective dose of from about 1 mg.-8 mg. of the base form of antazoline phosphate thereto. Such a treatment provides a therapeutically useful reduction in intraocular pressure for a period of time up to about three hours.

Aqueous ophthalmic solutions used in accordance with this invention may be formulated, for example, in accord with the procedures set forth in Chapter 83 of Remington's Pharmaceutical Sciences, 14th Edition, Mack Publishing Company. Such ophthalmic solutions are sterile and may contain a bacteriological preservative to maintain sterility during use. The quaternary ammonium bacteriostats such as benzalkonium chloride are satisfactory for this purpose. An antioxidant may also be employed if desired. By way of example, suitable antioxidants include sodium bisulfite, N-acetylcysteine salts, sodium ascorbate and other water soluble ophthalmologically acceptable antioxidants known to the pharmaceutical art.

In addition to antazoline phosphate, the other substantially non-toxic or non-irritating antazoline salts which may be topically administered according to this invention include those derived from organic or inorganic acids such as hydrochloric, hydrobromic, sulfuric, phosphoric, methanesulfonic, acetic, citric, malic, succinic, lactic, tartaric, benzoic acids and the like.

Ointments employed in practicing the present invention may be prepared utilizing known pharmaceutical techniques with conventional petrolatum vehicles.

It should be apparent that the practice of this invention includes other known means of topically administering therapeutically effective amounts of antazoline phosphate, for example, to mammalian eyes in order to reduce intraocular pressure. Such means will include ocular inserts which may be placed so that they are retained in contact with the surface of the eye and diffuse an effective, intraocular pressure lowering dose of antazoline phosphate to the eye over a prolonged period of time.

Therapeutically effective amounts of antazoline and/or its pharmaceutically acceptable salts may also be administered by the oral route.

The following example and tables will further illustrate the invention.

EXAMPLE

The following procedure was followed in determining the effectiveness of antazoline phosphate in reducing intraocular pressure in rabbits.

Healthy male New Zealand albino rabbits weighing between about 2.5 and 4.0 kg. each were restrained in stocks and isolated from food or water. A one hour acclimation period was permitted prior to testing. Drug solutions were prepared by dissolving the test drug in aqueous solution to the desired concentration, and 0.2 mg. of the test solution was instilled to one eye of each rabbit. The contralateral eye thereof, which served as the control eye during the course of the experiment, was left untreated. Pre-treatment measurements were made of normal intraocular pressure followed by post-treatment measurements at hourly intervals during a period of 1 to 3 or 4 hours. By comparing the change of intraocular pressure in the test eye to the contralateral eye which served as the control, the measure of reduction, i.e., the effectiveness of the test drug as an intraocular pressure lowering agent, was obtained. The intraocular pressure measurements were performed using a Bausch & Lomb Applamatic Tonometer. The results are presented below.

In Table I the data clearly establish that antazoline phosphate reduces intraocular pressure in the rabbit eye at several concentrations; the only variance being in the duration of activity.

In Table II, the data show that of the six antihistamine drugs tested, only antazoline phosphate caused an appreciable lowering of intraocular pressure in test eyes. Tripelennamine HCl caused a mild, transitory increase in mean intraocular pressure; instillation of diphenhydramine HCl resulted in a moderate bilateral increase in an intraocular pressure; and the group including dimenhydrinate, methapyrilene HCl, cyclizine HCl and chlorpheniramine maleate, all were found to elicit no change in intraocular pressure.

TABLE I
EFFECT OF VARIOUS DOSES OF ANTAZOLINE PHOSPHATE ON INTRAOCULAR PRESSURE (mmHg) IN RABBITS[a]

| Conc. | | Pre-Drug | | Time Post-Drug | | | | | | | |
|---|---|---|---|---|---|---|---|---|---|---|---|
| | | | | 1 Hr. | | 2 Hr. | | 3 Hr. | | 4 Hr. | |
| | | C[b] | T[c] | C | T | C | T | C | T | C | T |
| 0.5% | Mean | 9.0 | 9.3 | 8.8 | 7.3 | 9.3 | 8.8 | 9.3 | 9.3 | — | — |
| | ±S.E. | 0.6 | 0.3 | 0.6 | 0.3 | 0.3 | 0.2 | 0.3 | 0.3 | — | — |
| | % Change from Pre-Drug Value | | | −2 | −22 | +3 | −5 | +3 | 0 | — | — |
| 1.0% | Mean | 9.7 | 9.7 | 9.7 | 7.7 | 9.7 | 7.5 | 10.3 | 8.8 | — | — |
| | ±S.E. | 0.9 | 0.9 | 0.9 | 0.3 | 0.3 | 0.3 | 0.3 | 0.4 | — | — |
| | % Change from Pre-Drug Value | | | 0 | −21 | 0 | −23 | +6 | −9 | — | — |
| 2.0% | Mean | 10.3 | 10.3 | 10.2 | 8.3 | 10.7 | 8.3 | 10.3 | 9.0 | 11.0 | 10.7 |
| | ±S.E. | 0.7 | 0.7 | 0.6 | 0.3 | 0.3 | 0.4 | 0.3 | 0.6 | 0.6 | 0.3 |
| | % Change from Pre-Drug Value | | | −1 | −19 | +4 | −19 | 0 | −13 | +7 | +4 |
| 4.0% | Mean | 11.0 | 11.0 | 10.8 | 8.0 | 10.7 | 8.7 | 10.7 | 9.0 | 12.0 | 11.7 |
| | ±S.E. | 0.0 | 0.0 | 0.2 | 0.6 | 0.3 | 0.7 | 0.3 | 0.6 | 0.6 | 1.2 |
| | % Change from Pre-Drug Value | | | −2 | −27 | −3 | −21 | −3 | −18 | +9 | +6 |

[a] 3 animals for each concentration
[b] C = control eye
[c] T = test eye

TABLE II
COMPARATIVE EFFECTS OF TOPICALLY ADMINISTERED ANTIHISTAMINES[a] ON INTRAOCULAR PRESSURE (mmHg) IN RABBITS[a]

| Drug | Pre-Drug | | Post-Drug | | | | | |
|---|---|---|---|---|---|---|---|---|
| | | | 1 Hr. | | 2 Hr. | | 3 Hr. | |
| | T[b] | C[c] | T | C | T | C | T | C |
| Antazoline phosphate Mean | 11.2 | 8.8 | 11.2 | 9.3 | 11.0 | 10.0 | 11.2 | |
| % Change from Pre-Drug | | | −21.4 | 0.0 | −16.8 | −1.8 | −10.7 | 0.0 |
| Dimenhydrinate Mean | 11.0 | 11.0 | 10.7 | 10.7 | 11.2 | 11.2 | 11.5 | 11.2 |
| % Change from Pre-Drug | | | −2.7 | −2.7 | +1.8 | +1.8 | +4.5 | +1.8 |
| Diphenylhydramine hydrochloride Mean | 11.7 | 11.7 | 12.7 | 12.5 | 13.0 | 12.5 | 13.7 | 13.7 |
| % Change from Pre-Drug | | | +8.5 | +6.8 | +11.1 | +6.8 | +17.1 | +17.1 |
| Tripelennamine hydrochloride Mean | 10.0 | 10.0 | 11.3 | 10.2 | 10.2 | 9.8 | 10.2 | 10.0 |
| % Change from Pre-Drug | | | +13.0 | +2.0 | +2.0 | −2.0 | +2.0 | 0.0 |
| Methapyrilene hydrochloride Mean | 11.2 | 11.3 | 11.8 | 11.3 | 11.0 | 11.2 | 11.7 | 11.7 |
| % Change from Pre-Drug | | | +5.4 | 0.0 | −1.8 | −0.9 | +4.5 | +3.5 |
| Chlorpheniramine maleate Mean | 9.8 | 10.0 | 9.8 | 9.8 | 9.5 | 9.8 | 10.2 | 10.3 |
| % Change from | | | 0.0 | −2.0 | −3.1 | −2.0 | +4.1 | +3.0 |

TABLE II-continued

COMPARATIVE EFFECTS OF TOPICALLY ADMINISTERED ANTIHISTAMINES[a] ON INTRAOCULAR PRESSURE (mmHg) IN RABBITS[d]

| Drug | Pre-Drug T[b] | Pre-Drug C[c] | Post-Drug 1 Hr. T | 1 Hr. C | 2 Hr. T | 2 Hr. C | 3 Hr. T | 3 Hr. C |
|---|---|---|---|---|---|---|---|---|
| Pre-Drug Cyclizine hydrochloride Mean | 10.7 | 10.7 | 11.3 | 10.5 | 11.3 | 10.5 | 11.2 | 10.7 |
| % Change from Pre-Drug | | | +5.6 | −1.9 | +5.6 | −1.9 | +4.7 | 0.0 |
| Promethazine hydrochloride Mean | 11.7 | 11.7 | 12.7 | 11.8 | 12.3 | 11.7 | 11.3 | 11.5 |
| % Change from Pre-Drug | | | +8.5 | +0.9 | +5.1 | 0.0 | −3.4 | −1.7 |

[a] 2% aqueous solution
[b] T = test eye
[c] C = control eye
[d] eight groups of 3 animals in each group

We claim:

1. A method for reducing intraocular pressure in mammals having intraocular hypertension comprising topically administering to a mammilian eye an effective amount for reducing intraocular pressure of a composition comprising antazoline phosphate and a non-toxic, pharmaceutically acceptable, ophthalmological carrier.

2. The method of claim 1 wherein said composition comprises an aqueous solution containing a molar amount of antazoline phosphate equivalent to about 0.5% to about 4.0% by weight of antazoline.

3. The method of claim 2 wherein said composition further contains about 0.9% by weight sodium chloride.

UNITED STATES PATENT OFFICE
CERTIFICATE OF CORRECTION

Page 1 of 2

Patent No. 4,097,577          Dated   June 27, 1978

Inventor(s) HARRY SALEM and DOMINGO M. AVIADO

It is certified that error appears in the above-identified patent and that said Letters Patent are hereby corrected as shown below:

TABLE I, on the line between "% Change from" and "40% Mean" insert -- Pre-Drug Value---

TABLE II should read as follows:

TABLE II
COMPARATIVE EFFECTS OF TOPICALLY ADMINISTERED ANTIHISTAMINES[a] ON INTRAOCULAR PRESSURE (mmHg) IN RABBITS[d]

| Drug | Pre-Drug | | Post-Drug | | | | | |
| | | | 1 Hr. | | 2 Hr. | | 3 Hr. | |
| | T[b] | C[c] | T | C | T | C | T | C |
|---|---|---|---|---|---|---|---|---|
| Antazoline phosphate Mean | 11.2 | 11.2 | 8.8 | 11.2 | 9.3 | 11.0 | 10.0 | 11.2 |
| % Change from Pre-Drug | | | −21.4 | 0.0 | −16.8 | −1.8 | −10.7 | 0.0 |
| Dimenhydrinate Mean | 11.0 | 11.0 | 10.7 | 10.7 | 11.2 | 11.2 | 11.5 | 11.2 |
| % Change from Pre-Drug | | | −2.7 | −2.7 | +1.8 | +1.8 | +4.5 | +1.8 |
| Diphenylhydramine hydrochloride Mean | 11.7 | 11.7 | 12.7 | 12.5 | 13.0 | 12.5 | 13.7 | 13.7 |
| % Change from Pre-Drug | | | +8.5 | +6.8 | +11.1 | +6.8 | +17.1 | +17.1 |
| Tripelennamine hydrochloride Mean | 10.0 | 10.0 | 11.3 | 10.2 | 10.2 | 9.8 | 10.2 | 10.0 |
| % Change from Pre-Drug | | | +13.0 | +2.0 | +2.0 | −2.0 | +2.0 | 0.0 |
| Methapyrilene hydrochloride Mean | 11.2 | 11.3 | 11.8 | 11.3 | 11.0 | 11.2 | 11.7 | 11.7 |
| % Change from Pre-Drug | | | +5.4 | 0.0 | −1.8 | −0.9 | +4.5 | +3.5 |
| Chlorpheniramine maleate Mean | 9.8 | 10.0 | 9.8 | 9.8 | 9.5 | 9.8 | 10.2 | 10.3 |
| % Change from Pre-Drug | | | 0.0 | −2.0 | −3.1 | −2.0 | +4.1 | +3.0 |

UNITED STATES PATENT OFFICE
CERTIFICATE OF CORRECTION

Patent No. 4,097,577   Dated June 27, 1978

Inventor(s) HARRY SALEM and DOMINGO M. AVIADO

It is certified that error appears in the above-identified patent and that said Letters Patent are hereby corrected as shown below:

(Page 2)

TABLE II - continued should read as follows:

TABLE II-continued

COMPARATIVE EFFECTS OF TOPICALLY ADMINISTERED ANTIHISTAMINES[a] ON INTRAOCULAR PRESSURE (mmHg) IN RABBITS[d]

| Drug | Pre-Drug | | Post-Drug | | | | | |
|---|---|---|---|---|---|---|---|---|
| | | | 1 Hr. | | 2 Hr. | | 3 Hr. | |
| | T[b] | C[c] | T | C | T | C | T | C |
| Cyclizine hydrochloride | | | | | | | | |
| Mean | 10.7 | 10.7 | 11.3 | 10.5 | 11.3 | 10.5 | 11.2 | 10.7 |
| % Change from Pre-Drug | | | +5.6 | −1.9 | +5.6 | −1.9 | +4.7 | 0.0 |
| Promethazine hydrochloride | | | | | | | | |
| Mean | 11.7 | 11.7 | 12.7 | 11.8 | 12.3 | 11.7 | 11.3 | 11.5 |
| % Change from Pre-Drug | | | +8.5 | +0.9 | +5.1 | 0.0 | −3.4 | −1.7 |

[a] 2% aqueous solution
[b] T = test eye
[c] C = control eye
[d] eight groups of 3 animals in each group Signed and Sealed this Third Day of April 1979

[SEAL]

Attest:

RUTH C. MASON
Attesting Officer

DONALD W. BANNER
Commissioner of Patents and Trademarks